United States Patent [19]

Chibata et al.

[11] 4,160,697

[45] Jul. 10, 1979

[54] METHOD FOR PURIFICATION OF CRUDE UROKINASE

[75] Inventors: Ichiro Chibata, Suita; Toshio Kakimoto, Minamikawachi; Yoshiaki Kakie, Takatsuki; Takeji Shibatani, Kobe; Noriyuki Nishimura, Nara, all of Japan

[73] Assignee: Tanabe Seiyaku Co., Ltd., Osaka, Japan

[21] Appl. No.: 889,385

[22] Filed: Mar. 23, 1978

[30] Foreign Application Priority Data

Apr. 9, 1977 [JP] Japan .................................. 52-40683
Apr. 28, 1977 [JP] Japan .................................. 52-49634
Sep. 30, 1977 [JP] Japan .................................. 52-118321

[51] Int. Cl.$^2$ ............................................. C07G 7/026
[52] U.S. Cl. ....................................................... 435/194
[58] Field of Search ........................................ 195/66 B

[56] References Cited

U.S. PATENT DOCUMENTS

| | | | |
|---|---|---|---|
| 3,256,158 | 6/1966 | White .................................. | 195/66 B |
| 3,957,582 | 5/1976 | Stried et al. ......................... | 195/66 B |
| 4,025,390 | 5/1977 | Urakawa et al. ..................... | 195/66 B |

Primary Examiner—Lionel M. Shapiro
Attorney, Agent, or Firm—Bierman & Bierman

[57] ABSTRACT

An aqueous solution of crude urokinase is contacted with a cross-linked diethylaminoethyl-agarose to have pyrogens adsorbed thereon. The effluent is then contacted with a water-insoluble, hydrophilic polysaccharide having a group of the formula:

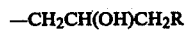

$$-CH_2CH(OH)CH_2R$$

wherein R is sulfothio, sulfo or p-sulfophenylamino, and the urokinase adsorbed is eluted from said polysaccharide. Pyrogen-free urokinase is thereby obtained in a high purity as the eluate.

32 Claims, No Drawings

METHOD FOR PURIFICATION OF CRUDE UROKINASE

BACKGROUND OF THE INVENTION

This invention relates to a method for purification of crude urokinase. More particularly, it relates to a method of preparing urokinase of high potency free of pyrogens.

Urokinase is a protein which is found in human urine in trace amounts. It stimulates the production in the blood of the clot-dissolving proteolytic enzyme, plasmin, and is useful in the treatment of certain circulatory disorders such as those which tend to cause the formation of blood clots in the cardiovascular or peripheral vascular systems.

Urokinase has been obtained from human urine by adsorption thereof on silica gel, activated diatomaceous earth, glass bead, aluminum magnesium silicate and so forth. However, urokinase obtained by such treatment is not satisfactory for the medicinal use because it still contains impurities such as pyrogens and clot-promoting substances (e.g., thromboplastin). In this connection, various methods for purification or urokinase have been known. For example, U.S. Pat. Nos. 3,256,158 and 3,957,582 disclose that purification of urokinase may be performed by contacting an aqueous solution of crude urokinase with a cross-linked dextran or a cross-linked diethylaminoethyl-dextran to have urokinase adsorbed thereon, eluting the adsorbed urokinase with a phosphate buffer solution from said dextran, and then recovering urokinase from the eluate. It has also been known that crude urokinase is purified by treating an aqueous solution thereof with Amberlite IRC-50, DEAE-cellulose, Sephadex G-50 and so forth.

SUMMARY OF THE INVENTION

We have now found that a water-insoluble, hydrophilic polysaccharide having a group of the formula:

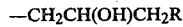

wherein R is sulfothio, sulfo or p-sulfophenylamino, has a specific affinity to urokinase and crude urokinase can be readily purified by contacting it with said polysaccharide. Urokinase can be adsorbed on the above-mentioned O-(3-substituted-2-hydroxypropyl)-polysaccharide quite specifically and reversibly, while pyrogens and other impurities are not adsorbed thereon. We have also found that a cross-linked diethylaminoethyl-agarose adsorbs pyrogens but not urokinase, and therefore in carrying out the purification of crude urokinase it is preferred to treat said crude urokinase with said agarose prior to bringing it into contact with the above-mentioned O-(3-substituted-2-hydroxypropyl)-polysaccharide.

An object of the present invention is to provide a simple and expeditious method for preparing urokinase of high potency free from pyrogens and other impurities. Another object of the invention is to provide a method for obtaining urokinase of highest purity from a crude urokinase solution so that the danger of a pyrogenic response is eliminated when such urokinase is injected intravenously into a living host. Other objects of the invention will be clearly observed from the description which follows.

The term "hydrophilic" as used herein means that the polysaccharide is made wettable or swellable in water but not substantially soluble therein.

DETAILED DESCRIPTION OF THE INVENTION INCLUDING PREFERRED EMBODIMENTS

According to the present invention, pyrogen-free urokinase can be prepared in a high yield by contacting an aqueous solution of crude urokinase with a water-insoluble, hydrophilic polysaccharide having a group of the formula:

wherein R is the same as defined above, to have urokinase adsorbed thereon, and then eluting the adsorbed urokinase from said O-(3-substituted-2-hydroxypropyl)-polysaccharide.

Examples of the O-(3-substituted-2-hydroxypropyl)-polysaccharide (i.e., 3-substituted-2-hydroxypropyl ethers of polysaccharide) which are employed in the present invention include O-(3-sulfothio-2-hydroxypropyl)-cellulose, O-(3-sulfothio-2-hydroxypropyl)-agarose, O-(3-sulfothio-2-hydroxypropyl)-dextran cross-linked with epichlorohydrin, O-(3-sulfo-2-hydroxypropyl)-cellulose, O-(3-sulfo-2-hydroxypropyl)-agarose, O-(3-sulfo-2-hydroxypropyl)dextran cross-linked with epichlorohydrin, O-[3-(p-sulfophenylamino)-2-hydroxypropyl]-cellulose, O-[3-(p-sulfophenylamino)-2-hydroxypropyl]-agarose, O-[3-(p-sulfophenylamino)-2-hydroxypropyl]-dextran cross-linked with epichlorohydrin, and the like. Suitable O-(3-substituted-2-hydroxypropyl)-polysaccharide of the invention should contain 100 to 800 μ moles, especially 300 to 650 μ moles, of 3-substituted-2-hydroxypropyl group per g (dried form) of the polysaccharide.

O-(3-substituted-2-hydroxypropyl)-polysaccharide as described above may be prepared by reacting a water-insoluble, hydrophilic polysaccharide with epichlorohydrin, and reacting the epichlorohydrin-activated polysaccharide with alkali metal thiosulfate, alkali metal hydrogensulfite, alkali metal sulfite or sulfanilic acid. The above-mentioned reactions are shown by the following scheme:

(1) Activation of polysaccharide:

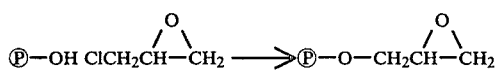

(2) Synthesis of O-(3-substituted-2-hydroxypropyl)-polysaccharide:

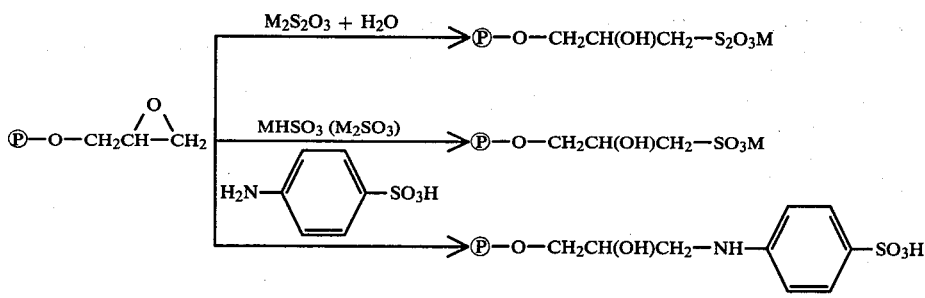

wherein Ⓟ—OH is a water-insoluble, hydrophilic polysaccharide and M is an alkali metal.

The activation of the polysaccharide is accomplished in accordance with the method described in Acta Chimica Scandinavia B29, No.4, pp. 471–474 (1975). Namely, said activation is preferably carried out by reacting the polysaccharide with epichlorohydrin at a temperature of 20° to 70° C., especially 40° to 60° C., in an aqueous solvent (e.g., an aqueous sodium hydroxide solution). Suitable amounts of epichlorohydrin which is employed in the activation are 0.05 to 15 ml, especially 0.5 to 10 ml, per g of the polysaccharide. The polysaccharides which are used in the above-mentioned reaction include, for example, cellulose, agarose and a cross-linked dextran. Among them, agarose and the cross-linked dextran are commercially available under the trade name "Sepharose" and "Sephadex" (Pharmacia Fine Chemicals of Uppsala, Sweden), respectively. The epichlorohydrin-activated polysaccharide obtained above is then reacted with alkali metal thiosulfate (e.g., sodium thiosulfate), alkali metal hydrogensulfite (e.g., sodium hydrogensulfite), alkali metal sulfite (e.g., sodium sulfite) or sulfanilic acid. This reaction is preferably carried out at a temperature of 10° to 50° C., especially 10° to 30° C., in an aqueous solvent (e.g., water, a buffer solution). It is preferred to carry out the reaction at a pH of 4 to 10.

In carrying out the purification step of the present invention, the crude urokinase solution may be, if required, contacted with a cross-linked diethylaminoethyl-agarose to remove pyrogens therefrom before it is brought into contact with the O-(3-substituted-2-hydroxypropyl)-polysaccharide. The cross-linked diethylaminoethyl (i.e., DEAE) -agarose which is employed for this purpose may be prepared by conventional diethylaminoethylation of a cross-linked agarose [cf. J. Am. Chem. Soc., 78, pages 751–755 (1956)]. Such cross-linked DEAE-agarose is commercially available under the trade name "DEAE-Sepharose CL-6B" (Pharmacia Fine Chemicals of Uppsala, Sweden), which is a swollen beads of a basic anion exchange resin and shows an exchange capacity of 13±2 meq/100 ml [1.54±0.24 meq/g(dried form)]. The adsorption of pyrogens on the cross-linked DEAE-agarose (i.e., cross-linked diethyl-aminoethyl-agarose) is readily carried out by contacting the aqueous solution of crude urokinase with the cross-linked DEAE-agarose. For example, the cross-linked DEAE-agarose is suspended in the aqueous crude urokinase solution, and the suspension is stirred for a sufficient period of time. It is preferred to equilibrate the cross-linked DEAE-agarose with a suitable buffer solution (e.g., phosphate buffer solution) prior to the adsorption step. An aqueous crude urokinase solution (pH 6 to 9), the specific electric conductivity of which is adjusted to not higher than 15 m mho/cm, especially 2 to to 10 m mho/cm, is preferably employed in this step. After pyrogens is adsorbed on the cross-linked DEAE-agarose, an aqueous urokinase solution which is substantially free of pyrogens may be separated by filtration, centrifugation or decantation. Alternatively, the adsorption of pyrogens on said cross-linked DEAE-agarose may be carried out by a column method. For example, the cross-linked DEAE-agarose is packed into a column, and an aqueous solution of crude urokinase (the specific conductivity of which is adjusted to not higher than 15 m mho/cm, especially to 2 to 10 m mho/cm) is passed through the column. An aqueous urokinase solution which is substantially free of pyrogens is obtained as the effluent.

Purification of an aqueous crude urokinase solution (or the crude urokinase solution partially purified with the cross-linked DEAE-agarose) can be accomplished by contacting said aqueous crude urokinase solution with the O-(3-substituted-2-hydroxypropyl)-polysaccharide to have urokinase adsorbed thereon. For example, the O-(3-substituted-2-hydroxypropyl)-polysaccharide is suspended in the aqueous crude urokinase solution, and the suspension is stirred for a sufficient period of time. It is preferred to equilibrate the polysaccharide with a suitable buffer solution (e.g., phosphate buffer solution) prior to the adsorption step. The aqueous crude urokinase solution (pH 3 to 9), the specific electric conductivity of which is adjusted to not higher than 15 m mho/cm, especially to 2 to 10 m mho/cm, is preferably employed for this purpose. Moreover, when the aqueous crude urokinase solution shows a specific electric conductivity higher than 15 m mho/cm, it is preferred that the solution is diluted with a suitable solvent (e.g., water) so that the specific electric conductivity thereof is adjusted to not higher than 15 m mho/cm. After urokinase is adsorbed on the O-(3-substituted-2-hydroxypropyl)-polysaccharide, said polysaccharide having adsorbed urokinase thereon may be recovered in conventional manners, for example, by filtration, centrifugation or decantation and, if required, may be washed with an aqueous solution (pH 3 to 9) having a specific electric conductivity not higher than 15 m mho/cm, especially the specific electric conductivity of 1 to 12 m mho/cm. By washing the O-(3-substituted-2-hydroxypropyl)-polysaccharide pyrogens and other impurities are removed from said polysaccharide, while urokinase remains adsorbed thereon.

The subsequent elution step is carried out by contacting the O-(3-substituted-2-hydroxypropyl)-polysaccharide with an eluting solvent. For example, said polysaccharide is suspended in the eluting solvent and the suspension is stirred for a sufficient period of time. An aqueous solution (pH 3 to 9) having a specific electric conductivity not lower than 20 m mho/cm, especially a specific electric conductivity of 30 to 100 m mho/cm, is preferably employed as the eluting solvent. Moreover, a phosphate buffer solution, a carbonate buffer solution, a tris(hydroxymethyl)aminomethane buffer solution, an aqueous sodium chloride solution and the like are suitable as the eluting solvent.

Alternatively, the above-mentioned two steps [i.e., adsorption or urokinase on the O-(3-substituted-2-hydroxypropyl)-polysaccharide and elution of urokinase from said polysaccharide] may be carried out by a column method. For example, the O-(3-substituted-2-hydroxypropyl)-polysaccharide is charged into a column. An aqueous crude solution (pH 3 to 9), the specific electric conductivity of which is adjusted to not higher than 15 m mho/cm, especially to 2 to 10 m mho/cm, is introduced into the column. The column is then washed with an aqueous solution (pH 3 to 9) having a specific electric conductivity not higher than 15 m mho/cm, especially a specific electric conductivity of 1 to 12 m mho/cm. After washing the column, the eluting solvent as mentioned above is passed through the column at a suitable flow rate to liberate urokinase therefrom. An aqueous urokinase solution is thereby obtained as the eluate.

Urokinase purified and recovered by the method of the present invention has a potent urokinase activity and is substantially free of pyrogens.

Practical and presently-preferred embodiments of the present invention are illustratively shown in the following Examples. Throughout the Examples, urokinase activity has been estimated in terms of "international units" defined in A. J. Johnson, et al's. Thromb. Diath. Haemorrh. (Stuttg.), 21, 259 (1969). Said activity has also been assayed by the fibrin plate method described in J. Ploug, et al's. Biochim. Biophys. Acta, 24, 278 (1957). On the other hand, pyrogenicity has been evaluated by the Pyrogen Test described in the Japanese Pharmacopoeia, 9th Edition, pgs. 681–682 (1976). Namely, a sample solution is dialyzed overnight against pyrogen-free distilled water and the dialyzed solution is injected intravenously into each of three rabbits. In this experiment, if no rabbit shows an individual rise in temperature of 0.6° C. or more above its respective control temperature, and if the sum of the three temperature rises does not exceed 1.4° C., the sample solution meets the requirements for the absence of pyrogens.

EXAMPLE 1

10 g of cellulose powder are suspended in 80 ml of an aqueous 25% sodium hydroxide solution. The suspension is allowed to stand in ice-water for 30 minutes under stirring at intervals. 420 ml of water and 50 ml of epichlorohydrin are added to the suspension, and the mixture is stirred vigorously at 50° to 60° C. for 30 minutes. After the reaction is completed, the precipitates are collected by filtration and washed with water.

The epichlorohydrin-activated cellulose thus obtained is suspended in 200 ml of an aqueous 1 M sodium thiosulfate solution, and the suspension is stirred at room temperature for one hour. The suspension is kept at a pH of 5 to 7 with 0.1 N hydrochloric acid during the reaction. After the reaction is completed, the precipitates are collected by filtration and then washed with water. 9.5 g (dried form) of O-(3-sulfothio-2-hydroxypropyl)-cellulose are obtained.

The content of 3-sulfothio-2-hydroxypropyl group: 320 μmoles/g (dried form)

EXAMPLE 2

20 g of agarose (manufactured by Pharmacia Fine Chemicals of Uppsala, Sweden under the trade name "Sepharose 6B") are suspended in 80 ml of an aqueous 1 N sodium hydroxide solution. 10 ml of epichlorohydrin are added to the suspension, and the mixture is stirred vigorously at room temperature for 24 hours. After the reaction is completed, the precipitates are collected by filtration and washed with water.

The epichlorohydrin-activated agarose thus obtained is suspended in 100 ml of an aqueous 1 M. sodium thiosulfate solution, and the suspension is stirred at room temperature for one hour. The suspension is kept at a pH of 5 to 7 with 0.1 N hydrochloric acid during the reaction. After the reaction is completed, the precipitates are collected by filtration and then washed with water. 19 g (dried form) of O-(3-sulfothio-2-hydroxypropyl)-agarose are obtained.

The content of 3-sulfothio-2-hydroxypropyl group: 550 μ moles/g (dried form)

EXAMPLE 3

10 g of dextran cross-linked with epichlorohydrin (manufactured by Pharmacia Fine Chemicals of Uppsala, Sweden under the trade name "Sephadex G-50") are suspended in 200 ml of an aqueous 1 N sodium hydroxide solution. 20 ml of epichlorohydrin are added to the suspension, and the mixture is stirred vigorously at room temperature for 5 hours. After the reaction is completed, the precipitates are collected by filtration and washed with water.

The cross-linked epichlorohydrin-activated dextran thus obtained is suspended in 200 ml of an aqueous 1 M sodium thiosulfate solution. The suspension is stirred at room temperature for one hour. The suspension is kept at a pH of 5 to 7 with 0.1 N hydrochloric acid during the reaction. After the reaction is completed, the precipitates are collected by filtration and washed with water, 9.2 g (dried form) of a cross-linked O-(3-sulfothio-2-hydroxypropyl)-dextran are obtained.

The content of 3-sulfothio-2-hydroxypropyl group: 620 μ moles/g (dried form)

EXAMPLE 4

10 g of cellulose powder are suspended in 80 ml of an aqueous 25% sodium hydroxide solution. The suspension is allowed to stand in ice-water for 30 minutes, and 420 ml of water are added thereto. The mixture is further allowed to stand at 40° C. for 30 minutes. 100 ml of epichlorohydrin are added to the mixture, and said mixture is stirred vigorously at 40° C. for 60 minutes. After the reaction is completed, the precipitates are collected by filtration and washed with water.

The epichlorohydrin-activated cellulose thus obtained is suspended in 100 ml of an aqueous 2 M sodium hydrogensulfite solution. The suspension is adjusted to pH 7.0 with sodium hydroxide and allowed to stand at room temperature for 18 hours. After the reaction is completed, the precipitates are collected by filtration and then washed with water. 9.5 g (dried form) of O-(3-sulfo-2-hydroxypropyl)-cellulose are obtained.

The content of 3-sulfo-2-hydroxypropyl group: 550 μ moles/g (dried form)

EXAMPLE 5

30 g of agarose (manufactured by Pharmacia Fine Chemicals of Uppsala, Sweden under the trade name "Sepharose 6B") are suspended in 180 ml of an aqueous 1 N sodium hydroxide solution. 10 ml of epichlorohydrin are added to the suspension, and the mixture is stirred vigorously at room temperature for 24 hours. After the reaction is completed, the precipitates are collected by filtration and washed with water.

The epichlorohydrin-activated agarose thus obtained is suspended in 100 ml of a 2 M potassium carbonate buffer solution (pH 10) containing sulfanilic acid (sulfanilic acid content: 30 g/100 ml). The suspension is stirred at room temperature for 6 days. After the reaction is completed, the precipitates are collected by filtration and then washed with water. 28 g (dried form) of O-[3-(p-sulfophenylamino)-2-hydroxypropyl]-agarose are obtained.

The content of 3-(p-sulfophenylamino)-2-hydroxypropyl group:

600 $\mu$ moles/g (dried form)

EXAMPLE 6

10 g of dextran cross-linked with epichlorohydrin (manufactured by Pharmacia Fine Chemicals of Uppsala, Sweden under the trade name "Sephadex G-50") are suspended in 200 ml of an aqueous 1 N sodium hydroxide solution. 20 ml of epichlorohydrin are added to the suspension and the mixture is stirred vigorously at room temperature for 3 hours. After the reaction is completed, the precipitates are collected by filtration and washed with water.

The cross-linked epichlorohydrin-activated dextran thus obtained is suspended in 200 ml of a 2 M potassium carbonate buffer solution (pH 10) containing sulfanilic acid (sulfanilic acid content: 5 g/200 ml). The suspension is stirred at room temperature for 5 days. After the reaction is completed, the precipitates are collected by filtration and then washed with water. 9.6 g (dried form) of a cross-linked O-[3-(p-sulfophenylamino)-2-hydroxypropyl]-dextran are obtained.

The content of 3-(p-sulfophenylamino)-2-hydroxypropyl group:

450 $\mu$ moles/g (dried form)

EXAMPLE 7

(1) 40 ml of a cross-linked diethylaminoethyl-agarose (manufactured by Pharmacia Fine Chemicals of Uppsala, Sweden under the trade name "DEAE-Sepharose CL-6B") are charged into a column of 2.3 cm in diameter and 9.6 cm in height, and equilibrated with a 0.01 M phosphate buffer solution at pH 8.0. 300,000 units of crude urokinase (6,713 units/mg of protein) are dissolved in 80 ml of a 0.01 M phosphate buffer solution (pH 8.0, specific electric conductivity: 1.3 m mho/cm). The aqueous crude urokinase solution (specific electric conductivity: 6.5 m mho/cm) thus obtained is passed through the column of DEAE-Sepharose CL-6B, and the column is washed with 80 ml of a 0.01 M phosphate buffer solution containing 0.05 M of sodium chloride (pH 8.0, specific electric conductivity: 5 m mho/cm). The effluent and washings are combined. The combined solution (total volume: 160 ml) contains 291,000 units of urokinase and shows the specific activity of 20,500 units/mg of protein. Yield: 97%.

The urokinase solution obtained above, when administered to three rabbits at the dose of 3,000 units/kg, raises the temperature thereof by 0.15°, 0.10° and 0.10° only. This clearly shows that said urokinase solution is negative to the Pyrogen Test of the Japanese Pharmacopoeia, whereas the crude urokinase solution (i.e., the urokinase solution employed as the starting material) at 150 units/kg raises the temperature of three rabbits by 0.55°, 0.70° and 0.95°, respectively.

(2) 7 ml of O-(3-sulfothio-2-hydroxypropyl)-cellulose obtained in the same manner as described in Example 1 are charged into a column of 2.0 cm in diameter and 2.3 cm in height, and equilibrated with a 0.01 M phosphate buffer solution at ph 8.0. 160 ml of the urokinase solution (291,000 units, specific electric conductivity: 6.2 m mho/cm, pH 8.0) obtained in paragraph (1) are introduced into the column of O-(3-sulfothio-2-hydroxypropyl)-cellulose to have urokinase absorbed thereon. The column is washed with a 0.01 M phosphate buffer solution containing 0.1 M of sodium chloride (pH 8.0, specific electric conductivity: 10 m mho/cm), and then eluted with 30 ml of a 0.01 M phosphate buffer solution containing 0.5 M of sodium chloride (pH 8.0, specific electric conductivity: 45 m mho/cm). 2-ml fractions are obtained successively as the eluate and fraction No. 3 to 7 are combined. The urokinase eluate thus obtained contains 271,000 units of urokinase and shows the specific activity of 59,000 units/mg of protein. Yield: 93% [based on the urokinase solution obtained in paragraph (1) ].

The urokinase eluate passed the Pyrogen Test of the Japanese Pharmacopoeia at 3,000 units/kg with the temperature rise of 0.00°, 0.05° and 0.00°

EXAMPLE 8

(1) 40 ml of a cross-linked diethylaminoethyl-agarose (manufactured by Pharmacia Fine Chemicals of Uppsala, Sweden under the trade name "DEAE-Sepharose CL-6B") are charged into a column of 2.3 cm in diameter and 9.6 cm in height, and equilibrated with a 0.01 M phosphate buffer solution at pH 8.0. 300,000 units of crude urokinase (1,100 units/mg of protein) are dissolved in 80 ml of a 0.01 M phosphate buffer solution (pH 8.0, specific electric conductivity: 1.3 m mho/cm). The aqueous crude urokinase solution (specific electric conductivity:7 m mho/cm) thus obtained is passed through the column of DEAE-Sepharose CL-6B, and the column is washed with 80 ml of a 0.01 M phosphate buffer solution containing 0.05 M of sodium chloride (pH 8.0, specific electric conductivity: 5 m mho/cm). The effluent and washings are combined. The combined solution (total volume: 160 ml) contains 285,000 units of urokinase and shows the specific activity of 3,800 units/mg of protein. Yield: 95%.

The urokinase solution obtained above, when administered to three rabbits at the dose of 3,000 units/kg, raises the temperature thereof by 0.20°, 0.30° and 0.25°. This clearly shows that said urokinase solution is negative to the Pyrogen Test of the Japanese Pharmacopoeia, whereas the crude urokinase solution (i.e., the urokinase solution employed as the starting material) at 150 units/kg raises the temperature of three rabbits by 100°, 1.10° and 1.20°, respectively.

(2) 7 ml of O-(3-sulfothio-2-hydroxypropyl)-cellulose obtained in the same manner as described in Example 1 are packed in to a column of 2.0 cm in diameter and 2.3 cm in height, and equilibrated with a 0.01 M phosphate buffer solution at pH 8.0. 160 ml of the urokinase solution (285,000 units, specific activity: 3,800 units/mg of protein, pH 8.0, specific electric conductivity: 6 m mho/cm) obtained in paragraph (1) are introduced into the column of O-(3-sulfothio-2-hydroxypropyl)-cellulose to have urokinase adsorbed thereon. The column is washed with a 0.01 M phosphate buffer solution containing 0.1 M of sodium chloride (pH 8.0, specific electric conductivity: 10 m mho/cm), and then eluted with 30 ml of a 0.01 M phosphate buffer solution containing 0.5 M of sodium chloride (pH 8.0, specific electric conductivity: 45 m mho/cm). 2-ml fractions are obtained successively as the eluate and fraction No. 3 to 7 are combined. The urokinase eluate thus obtained contains 263,000 units of urokinase and shows the specific activity of 36,000 units/mg of protein. Yield: 92%.

The urokinase eluate passes the Pyrogen Test at 3,000 units/kg with the temperature rise of 0.10°, 0.05° and 0.05°.

EXAMPLE 9

10 ml of O-(3-sulfothio-2-hydroxypropyl)-cellulose obtained in the same manner as described in Example 1 are packed into a column of 1.3 cm in diameter and 7.3 cm in height, and equilibrated with a 0.01 M phosphate buffer solution at pH 7.0. 50,000 units of crude urokinase (5,500 units/mg of protein) are dissolved in 50 ml of a 0.01 M phosphate buffer solution (pH 7.0, specific electric conductivity: 1.3 m mho/cm). The aqueous crude urokinase solution (specific electric conductivity: 2.5 m mho/cm) thus obtained is introduced into the column of O-(3-sulfothio-2-hydroxypropyl)-cellulose. The column is washed with a 0.01 M phosphate buffer solution (pH 7.0, specific electric conductivity: 1.3 m mho/cm), and then eluted with 30 ml of a 0.01 M phosphate buffer solution containing 1 M of sodium chloride (pH 7.0, specific electric conductivity: 75 m mho/cm). 2-ml fractions are obtained successively as the eluate and fraction No. 3 to 7 are combined. The urokinase eluate thus obtained contains 44,000 units of urokinase and shows the specific activity of 40,000 units/mg of protein. Yield: 88%.

The urokinase eluate passes the Pyrogen Test at 3,000 units/kg with the temperature rise of 0.35°, 0.45° and 0.45°.

EXAMPLE 10

50,000 units of crude urokinase (5,500 units/mg of protein) are dissolved in 50 ml of a 0.01 M phosphate buffer solution (pH 7.0, specific electric conductivity: 1.3 m mho/cm). The aqueous crude urokinase solution (specific electric conductivity: 2.5 m mho/cm) thus obtained is treated in the same manner as described in Example 9 except that O-(3-sulfothio-2-hydroxypropyl)-agarose obtained in the same manner as described in Example 2 is used instead of O-(3-sulfothio-2-hydroxypropyl)-cellulose. The urokinase eluate thus obtained contains 41,000 units of urokinase and shows the specific activity of 32,000 units/mg of protein. Yield: 82%.

The urokinase eluate obtained above passes the Pyrogen Test at 3,000 units/kg.

EXAMPLE 11

50,000 units of crude urokinase (5,500 units/mg of protein) are dissolved in 50 ml of a 0.01 M phosphate buffer solution (pH 7.0, specific electric conductivity: 1.3 m mho/cm). The aqueous crude urokinase solution (specific electric conductivity: 2.5 m mho/cm) thus obtained is treated in the same mammer as described in Example 9 except that a cross-linked O-(3-sulfothio-2-hydroxypropyl)-dextran obtained in the same manner as described in Example 3 is used instead of O-(3-sulfothio-2-hydroxypropyl)-cellulose. The urokinase eluate thus obtained contains 40,000 units of urokinase and shows the specific activity of 35,500 units/mg of protein. Yield: 80%.

The urolinase eluate obtained above passes the Pyrogen Test at 3,000 units/kg.

EXAMPLE 12

50,000 units of crude urokinase (5,500 units/mg of protein) are dissolved in 50 ml of a 0.01 M phosphate buffer solution (pH 7.0, specific electric conductivity: 1.3 m mho/cm). The aqueous crude urokinase solution (specific electric conductivity: 2.5 m mho/m) thus obtained is treated in the same manner as described in Example 9 except that O-(3-sulfo-2-hydroxypropyl)-cellulose obtained in the same manner as described in Example 4 is used instead of O-(3-sulfothio-2-hydroxypropyl)-cellulose. The urokinase eluate thus obtained contains 45,000 units of urokinase and shows the specific activity of 30,000 units/mg of protein. Yield: 90%.

The urokinase eluate obtained above passes the Pyrogen Test at 3,000 units/kg.

EXAMPLE 13

50,000 units of crude urokinase (5,500 units/kg of protein) are dissolved in 50 ml of a 0.01 M phosphate buffer solution (pH 7.0, specific electric conductivity: 1.3 m mho/cm). The aqueous crude urokinase solution (specific electric conductivity: 2.5 m mho/cm) thus obtained is treated in the same mammer as described in Example 9 except that O-[3-(p-sulfophenylamino)-2-hydroxypropyl]-agarose obtained in the same manner as described in Example 5 is used instead of O-(3-sulfothio-2-hydroxypropyl)-cellulose. The urokinase eluate thus obtained contains 45,000 units of urokinase and shows the specific activity of 35,000 units/mg of protein. Yield: 90%.

The urokinase eluate obtained above passes the Pyrogen Test at 3,000 units/kg.

EXAMPLE 14

50,000 units of crude urokinase (5,500 units/mg of protein) are dissolved in 50 ml of a 0.01 M pHosphate buffer solution (pH 7.0, specific electric conductivity: 1.3 m mho/cm). The aqueous crude urokinase solution (specific electric conductivity: 2.5 m mho/cm) thus obtained is treated in the same manner as described in Example 9 except that a cross-linked O-[3-(p-sulfophenylamino)-2-hydroxypropyl]-dextran obtained in the same manner as described in Example 6 is used instead of O-(3-sulfothio-2-hydroxypropyl)-cellulose. The urokinase eluate thus obtained contains 44,000 units of urokinase and shows the specific activity of 38,000 units/mg of protein. Yield: 88%.

The urokinase eluate obtained above passes the Pyrogen Test at 3,000 units/kg.

What we claim is:

1. A method of purifying crude urokinase which comprises contacting an aqueous urokinase solution with a water-insoluble, hydrophilic polysaccharide having a group of the formula:

wherein R is sulfothio, sulfo or p-sulfophenylamino, to have urokinase adsorbed thereon, and eluting the adsorbed urokinase from said polysaccharide to recover urokinase.

2. The method of claim 1, wherein said aqueous urokinase solution has a specific electric conductivity not higher tha 15 m mho/cm, and the elution is carried out by contacting said polysaccharide with an aqueous solution of a specific electric conductivity not lower than 20 m mho/cm.

3. The method of claim 2, wherein the aqueous solution employed for said elution is selected from the group consisting of a phosphate buffer solution, a carbonate buffer solution, a tris(hydroxymethyl)aminomethane buffer solution and an aqueous sodium chloride solution.

4. The method of any one of claims 1 to 3, wherein said polysaccharide contains 100 to 800 μmoles of 3-substituted-2-hydroxypropyl group per g (dried from) of said polysaccharide.

5. The method of claim 4, wherein said polysaccharide is O-(3-sulfothio-2-hydroxypropyl)-polysaccharide.

6. The method of claim 4, wherein said polysaccharide is O-(3-sulfo-2-hydroxypropyl)-polysaccharide.

7. The method of claim 4, wherein said polysaccharide is O-[3-(p-sulfophenylamino)-2-hydroxypropyl]-polysaccharide.

8. The method of claim 5, wherein said O-(3-sulfothio-2-hydroxypropyl)-polysaccharide is selected from the group consisting of O-(3-sulfothio-2-hydroxypropyl)cellulose, O-(3-sulfothio-2-hydroxypropyl)-agarose and O-(3-sulfothio-2-hydroxypropyl)-dextran cross-linked with epichlorohydrin.

9. The method of claim 6, wherein said O-(3-sulfo-2-hydroxypropyl)-polysaccharide is selected from the group consisting of O-(3-sulfo-2-hydroxypropyl)-cellulose, O-(3-sulfo-2-hydroxypropyl)-agarose and O-(3-sulfo-2-hydroxypropyl)-dextran cross-linked with epichlorohydrin.

10. The method of claim 7, wherein said O-[3-(p-sulfophenylamino)-2-hydroxypropyl]-polysaccharide is selected from the group consisting of O-[3-(p-sulfophenylamino)-2-hydroxypropyl]-cellulose, O-[3-(p-sulfophenylamino)-2-hydroxypropyl]-agarose and O-[3-(p-sulfophenylamino)-2-hydroxpropyl]-dextran cross-linked with epichlorohydron.

11. A method of purifying crude urokinase which comprises contacting an aqueous urokinase solution (said solution having a specific electric conductivity of 2 to 10 m mho/cm) with a water-insoluble, hydrophilic polysaccharide having a group of the formula:

—CH$_2$CH(OH)CH$_2$R wherein R is sulfothio, sulfo or p-sulfophenylamino, to have urokinase adsorbed thereon, washing said polysaccharide with an aqueous solution of a specific electric conductivity of 1 to 12 m mho/cm, and then eluting the adsorbed urokinase from said washed polysaccharide with an aqueous solution of a specific electric conductivity of 30 to 100 m mho/cm to recover urokinase.

12. The method of claim 11, wherein the aqueous solution employed for said elution is selected from the group consisting of a phosphate buffer solution, a carbonate buffer solution, a tris(hydroxymethyl)aminomethane buffer solution and an aqueous sodium chloride solution.

13. The method of either one of claims 11 or 12, wherein said polysaccharide contains 300 to 650 μ moles of the 3-substituted-2-hydroxypropyl group per g (dried form) of said polysaccharide.

14. The method of claim 13, wherein said polysaccharide is O-(3-sulfothio-2-hydroxypropyl)-polysaccharide.

15. The method of claim 13, wherein said polysaccharide is O-(3-sulfo-2-hydroxypropyl)-polysaccharide.

16. The method of claim 13, wherein said polysaccharide is O-[3-(p-sulfophenylamino)-2-hydroxypropyl]-polysaccharide.

17. The method of claim 14, wherein said O-(3-sulfothio-2-hydroxypropyl)-polysaccharide is O-(3-sulfothio-2-hydroxypropyl)-cellulose.

18. A method of purifying crude urokinase which comprises contacting an aqueous urokinase solution with a cross-linked diethylaminoethyl-agarose, separating said urokinase solution from said agarose, contacting the separated urokinase solution with a water-insoluble, hydrophilic polysaccharide having a group of the formula:

—CH$_2$CH(OH)CH$_2$R wherein R is sulfothio, sulfo or p-sulfophenylamino, to have urokinase adsorbed thereon, and eluting the adsorbed urokinase from said polysaccharide to recover urokinase.

19. The method of claim 18, wherein said aqueous urokinase solution has a specific electric conductivity not higher than 15 m mho/cm, and the elution is carried out by contacting said polysaccharide with an aqueous solution of a specific electric conductivity not lower than 20 m mho/cm.

20. The method of claim 19, wherein the aqueous solution employed form said elution is selected from the group consisting of a phosphate buffer solution, a carbonate buffer solution, a tris(hydroxymethyl)aminomethane buffer solution and an aqueous sodium chloride solution.

21. The method of any one of claims 18 to 20, wherein said polysaccharide contains 100 to 800 μ moles of the 3-substituted -2-hydroxypropyl group per g (dried form) of said polysaccharide.

22. The method of claim 21, wherein said polysaccharide is O-(3 -sulfothio-2-hydroxypropyl)-polysaccharide.

23. The method of claim 21, wherein said polysaccharide is O-(3-sulfo-2-hydroxypropyl)-polysaccharide.

24. The method of claim 21, wherein said polysaccharide is O-[3-(p-sulfophenylamino)-2-hydroxypropyl]-polysaccharide.

25. The method of claim 22, wherein said O-(3-sulfothio-2-hydroxypropyl)-polysaccharide is O-(3-sulfothio-2-hydroxypropyl)-cellulose.

26. A method of purifying crude urokinase which comprises contacting an aqueous urokinase solution (said solution having a specific electric conductivity of 2 to 10 m mho/cm) with a cross-linked diethylaminoethyl-agarose, separating said urokinase solution from said agarose, contacting the separated urokinase solution with a water-insoluble, hydrophilic polysaccharide having a group of the formula:

—CH$_2$CH(OH)CH$_2$R wherein R is sulfothio, sulfo or p-sulfophenylamino, to have urokinase adsorbed thereon, washing said polysaccharide with an aqueous solution of a specific electric conductivity of 1 to 12 m mho/cm, and then eluting the adsorbed urokinase from said washed polysaccharide with an aqueous solution of a specific electric conductivity of 30 to 100 m mho/cm to recover urokinase.

27. The method of claim 26, wherein the aqueous solution employed for said elution is selected from the group consisting of a phosphate buffer solution, a carbonate buffer solution, a tris(hydroxymethyl)aminomethane buffer solution and an aqueous sodium chloride solution.

28. The method of either one of claims 26 or 27, wherein said polysaccharide contains 300 to 650 μ moles of the 3-substituted-2-hydroxypropyl group per g (dried form) of said polysaccharide.

29. The method of claim 28, wherein said polysaccharide is O-(3-sulfothio-2-hydroxypropyl)-polysaccharide.

30. The method of claim 28, wherein said polysaccharide is O-(3-sulfo-2-hydroxypropyl)-polysaccharide.

31. The method of claim 28, wherein said polysaccharide is O-[3-(p-sulfophenylamino)-2-hydroxypropyl]-polysaccharide.

32. The method of claim 29, wherein said O-(3-sulfothio-2-hydroxypropyl)-polysaccharide is O-(3-sulfothio-2-hydroxypropyl)-cellulose.

* * * * *